(12) United States Patent
Batista

(10) Patent No.: US 12,108,798 B2
(45) Date of Patent: Oct. 8, 2024

(54) MULTI-CHANNEL AND REVERSED AIRFLOW MOUTHPIECE FOR AN AEROSOL-GENERATING ARTICLE

(71) Applicant: PHILIP MORRIS PRODUCTS S.A., Neuchatel (CH)

(72) Inventor: Rui Nuno Batista, Morges (CH)

(73) Assignee: Philip Morris Products S.A., Neuchatel (CH)

( * ) Notice: Subject to any disclaimer, the term of this patent is extended or adjusted under 35 U.S.C. 154(b) by 456 days.

(21) Appl. No.: 17/600,744

(22) PCT Filed: Apr. 3, 2020

(86) PCT No.: PCT/EP2020/059532
§ 371 (c)(1),
(2) Date: Oct. 1, 2021

(87) PCT Pub. No.: WO2020/201495
PCT Pub. Date: Oct. 8, 2020

(65) Prior Publication Data
US 2022/0175043 A1    Jun. 9, 2022

(30) Foreign Application Priority Data
Apr. 3, 2019 (EP) .................................. 19166989

(51) Int. Cl.
*A24F 40/485* (2020.01)
*A24F 7/02* (2006.01)
*A24F 40/70* (2020.01)

(52) U.S. Cl.
CPC .............. *A24F 40/485* (2020.01); *A24F 7/02* (2013.01); *A24F 40/70* (2020.01)

(58) Field of Classification Search
CPC .......... A24F 40/485; A24F 7/02; A24F 40/20; A24F 40/10; A24F 40/40
See application file for complete search history.

(56) References Cited

U.S. PATENT DOCUMENTS 10,506,830 B2 * 12/2019 Li ........................... A24F 40/30
10,881,146 B2 * 1/2021 Qiu ......................... A24F 40/00
(Continued)

FOREIGN PATENT DOCUMENTS

CN     205 648 916     10/2016
CN     205 987 968     3/2017
(Continued)

OTHER PUBLICATIONS

Office Action issued in Japan for Application No. 2021-556263 dated Oct. 4, 2022 (13 pages). English translation included.
(Continued)

*Primary Examiner* — Hae Moon Hyeon
(74) *Attorney, Agent, or Firm* — Mueting Raasch Group

(57) ABSTRACT

The mouthpiece for an aerosol-generating article comprises a housing with an inlet end, configured to allow an aerosol to flow into the mouthpiece, an outlet end, configured to allow the aerosol to flow out of the mouthpiece, and an aerosol flow path extending between the inlet and the outlet end. The mouthpiece is formed such that the flow direction of the aerosol is reversed at least once between the inlet and the outlet end. The invention also concerns an aerosol-generating system comprising an aerosol-generating device and the mouthpiece, as well as a method for assembling the mouthpiece.

13 Claims, 6 Drawing Sheets

(56) References Cited

U.S. PATENT DOCUMENTS

| | | |
|---|---|---|
| 2016/0345630 A1* | 12/2016 | Mironov .............. A61M 11/042 |
| 2018/0007962 A1 | 1/2018 | Hunt |
| 2023/0147576 A1* | 5/2023 | Batista .................... A24F 40/48 |
| | | 131/328 |

FOREIGN PATENT DOCUMENTS

| | | | |
|---|---|---|---|
| CN | 205987968 U | * | 3/2017 |
| DE | 1 632 721 A1 | | 4/1971 |
| EP | 2 984 952 | | 2/2016 |
| GB | 1088217 | | 10/1967 |
| GB | 1088217 A | * | 10/1967 |
| JP | S59-55498 | | 4/1984 |
| JP | S60-3752 | | 2/1985 |
| JP | S6031294 | | 3/1985 |
| RU | 133694 | | 10/2013 |
| RU | 2607767 | | 1/2017 |
| WO | WO 2011/129701 | | 10/2011 |

OTHER PUBLICATIONS

Office Action issued in Russia for Application No. 2021122038 dated Dec. 2, 2021 (8 pages). English translation included.

PCT International Search Report and Written Opinion for PCT/EP2020/059532 dated May 26, 2020 (23 pages).

* cited by examiner

MULTI-CHANNEL AND REVERSED AIRFLOW MOUTHPIECE FOR AN AEROSOL-GENERATING ARTICLE

This application is a U.S. National Stage Application of International Application No. PCT/EP2020/059532 filed Apr. 3, 2020, which was published in English on Oct. 8, 2020, as International Publication No. WO 2020/201495 A1. International Application No. PCT/EP2020/059532 claims priority to European Application No. 19166989.4 filed Apr. 3, 2019.

INTRODUCTION

The present invention relates to a mouthpiece for an aerosol-generating article, an aerosol-generating system comprising the mouthpiece and the aerosol-generating article, and to a method for assembling the mouthpiece.

Today a number of different aerosol-generating systems are known in which inhalable vapor is generated in different ways. In the so-called e-vaping devices a liquid aerosol-forming substrate is vaporized by electrically powered heating devices. In heat-not-burn devices, a solid aerosol-forming substrate that may contain tobacco material is heated but not burned. These heat-not-burn devices may be electrically powered. There are also heat-not-burn systems in which heat is generated by combustion or chemical reactions.

In all these systems the aerosol-forming substrate is vaporized by the heating element and aerosol is subsequently formed. Aerosol formation, in particular droplet size, total particulate matter yield (TPM), aerosol temperature or homogeneity of the aerosol, depends upon multiple factors such as cooling of the air downstream of the aerosol-forming substrate and air pressure. Aerosol formation also depends on environmental conditions such as temperature, air pressure or humidity. Accordingly changes in average temperature and humidity levels may be relevant factors that affect aerosolization formation in aerosol-generating systems.

It would be desirable to provide a mouthpiece for an aerosol-generating system to improve aerosol generation.

It would be desirable to provide a mouthpiece for an aerosol-generating system which allows the aerosol-generating system to reach optimized aerosolization independent from the environmental or climate conditions.

It would be desirable to provide an adjustable mouthpiece that may be configured during use to influence aerosolization characteristics and to meet user preferences.

SUMMARY

According to an aspect of the invention there is provided a mouthpiece for an aerosol-generating article. The mouthpiece comprises a housing with an inlet end, configured to allow an aerosol to flow into the mouthpiece, and an outlet end, configured to allow the aerosol to flow out of the mouthpiece. An aerosol flow path extends between the inlet and the outlet end. The mouthpiece is formed such that the flow direction of the aerosol is reversed at least once between the inlet and the outlet end.

The mouthpiece of the present invention allows managing the air-flow from the aerosolization point of an aerosol-generating device towards the outlet of the mouthpiece. In this way optimal inhalation conditions may be obtained, enhancing all aspects of the generated aerosol such as droplet size, temperature, or total particulate matter yield. The specific airflow management pathways are using a plurality of fluid mechanics expansion factors along axial and radial air flow directions.

DETAILED DESCRIPTION

The mouthpiece may have any desired outer shape. Advantageously, the mouthpiece has an outer shape that corresponds to the outer shape of the aerosol-generating devices to which the mouthpiece is to be attached. For example, the mouthpiece may have a tubular or cylindrical outer shape.

The aerosol flow path of the mouthpiece may include a plurality of channels. The total length of the aerosol flow path is defined by the sum of the lengths of each individual channel. The channels may be arranged such that the total length of the aerosol flow path may be greater than the axial length of the mouthpiece. Thus, by the specific arrangement of the channels, an effective extension of the airflow path is achieved with respect to conventional mouthpieces with only one generally linear airflow channel. Extension of the airflow path enhances cooling and homogenization of the aerosol.

The channels may be tubular channels. The tubular channels may be co-axially arranged within the mouthpiece. The inlet end of the mouthpiece may be in direct fluid connection with a tubular channel that is arranged on along the central longitudinal axis of the mouthpiece. The airflow path may then continue through the one or more further co-axially arranged channels. The outermost of the co-axially arranged tubular channels is in direct fluid connection with the outlet end of the mouthpiece.

With the co-axial arrangement of the tubular channels a well-defined and symmetric airflow path through the mouthpiece is provided. Such symmetric design allows for optimal and repeatable inhalation conditions.

In embodiments of the mouthpiece the aerosol flow direction through the plurality of channels may differ. The aerosol flow direction through the plurality of channels may be reversed between each consecutively arranged aerosol flow channels. In this way the aerosol is guided multiple times through the mouthpiece from the inlet end to the outlet end, such that a significant extension of the airflow path is achieved.

Within the airflow path of the mouthpiece a plurality of expansion chambers may be formed. These expansion chambers may be formed in the transition areas between two consecutively arranged tubular channels. The expansion chambers affect the aerosol characteristics by temporarily expanding the airflow volume and by reversing the airflow direction. In this way a homogeneous aerosol with a desired particle size may be obtained.

The outermost tubular channel may extend to the outlet end of the mouthpiece, and may define an annular or ring-shaped outlet end of the mouthpiece.

The outlet end of the mouthpiece may have any other desired form and may be formed by the outer wall of the mouthpiece. The mouthpiece may comprise a cavity recessed from the outlet end of the mouthpiece. This cavity may also be denoted as a volumetric recess. Such volumetric recess may be regarded as a final expansion chamber of the airflow path. Accordingly, the volumetric recess may contribute to homogenization of the aerosol and in particular may facilitate cooling of the aerosol. A recessed outlet may enable to reach further enhanced aerosolization at the outlet end of the mouthpiece, and therefore different perception and satisfaction of the consumer.

The mouthpiece may comprise a central channel that extends from the inlet end and that radially diverges along the direction of the aerosol flow. The mouthpiece may further comprise at least two tubular channels that are co-axially arranged with respect to the central channel and that are in fluid communication with the central channel. The aerosol flow direction through these three channels may be reversed between each consecutively arranged aerosol flow channels. Accordingly, in the central channel, the direction of the airflow runs from the inlet end towards the outlet end. In the adjacent second tubular channel, the airflow direction is reversed and runs from the outlet and towards the inlet end. At the end of the second tubular channel airflow direction is again inverted, such that in the third tubular channel, the airflow direction is again directed towards the outlet end. At the end of the third tubular channel, the aerosol is discharged from the mouthpiece.

In this way the aerosol is guided multiple times through the mouthpiece from the inlet end to the outlet end, such that a significant extension of the airflow path is achieved.

The mouthpiece may be formed from any suitable material, such as polymeric materials. Suitable materials include food and/or medical grade polymeric compounds, in particular thermoplastic polyester elastomers (TPC-ETs), Polyoxymethylene Compounds (POM), High Density Polyethylene (HDPE), Low Density Polyethylene (LDPE), Polybutylene terephthalate (PBT), acrylic multipolymer, biodegradable polylactic acid (PLA) or cyclic olefin copolymer (COC).

The mouthpiece may be constructed from at least two main parts that can be axially inserted into each other. These two main parts may be formed such that when axially inserted into each other, the airflow path is performed between these two main parts.

The mouthpiece may be formed from an outer part and an inner part. The outer part may form a central inner channel and may comprise a tubular outer wall that at the same time forms the outer wall of the mouthpiece.

The inner part may have a hollow tubular shape with a side wall, one open end face and one closed end face. The inner part may be axially inserted into the outer part in such a way that the side wall of the inner part is located between the central channel and the outer wall of the outer part. In this way a second channel is formed between the sidewall of the inner part and the central channel. A third channel is performed between the sidewall of the inner part and the outer wall of the outer part. Thus, when the two parts are assembled, an airflow channel is formed from the inlet end through the central channel and further on through the second and third channel towards the outlet end of the mouthpiece. This two-part construction facilitates manufacture of a mouthpiece with a mazelike course of the airflow path.

This two-part construction allows manufacturing of the individual parts by conventional and well-known blow molding processes. Such processes may be more convenient to handle than other potential manufacturing techniques required for manufacturing a mouthpiece according to the present invention as an integral part.

The outer part may comprise the inlet end of the mouthpiece.

The inner part may be axially inserted from the outlet end side into the outer part. This allows the inner part to be inserted into and retracted from the outer part in a state where the outer part is attached to an aerosol-generating article. The inner part may be inserted into the outer part and retracted from the outer part without the need to disassemble the outer part from the aerosol-generating article. This enables an easy replacement of the inner part of the mouthpiece. This enables easy handling for a user.

The two main parts of the mouthpiece may have corresponding interlocking structures that engage with each other upon assembly such that a mouthpiece with predetermined dimensions may be obtained. In addition the interlocking structures assist in maintaining the mouthpiece in the assembled configuration. In particular, the interlocking structures are formed such as to prevent inadvertent disassembly of the mouthpiece during use.

The interlocking structures may comprise one or more fins and one or more intruded ring cavities that are provided at opposing surfaces of the main parts of the mouthpiece. Upon assembly each of the one or more fins provided on a surface of the one part engage with a corresponding intruded ring cavity provided on a surface of the other part of the mouthpiece. The fins may be provided at the outer surface of the side wall of the inner part, while the intruded ring cavities may be provided at the inner surface of the outer wall of the outer part.

The interlocking structures may be evenly distributed over the circumference of the two parts, such that after assembly the two parts are firmly held in a co-axially aligned position. To this end, the interlocking structures may be provided as one or more sets of interlocking structures. Each set may consist of three or more interlocking structures that are provided at the same axial position and are evenly distributed over the circumference of the two main parts of the mouthpiece. By providing two sets of interlocking structures, wherein each said comprises at least three interlocking structures, the two main parts can be reliably held in a predetermined orientation with respect to each other.

By configuring the interlocking structures in the form of corresponding fins and intruded ring cavities, a simple but reliable manufacture of a two-part mouthpiece is enabled. The connection between the interlocking structures can be configured such that an inadvertent disassembly of the mouthpiece is prevented, while an intended disassembly may be facilitated by controlled pulling apart of the two parts.

The interlocking structures may comprise additional sets of interlocking structure, such that the two main parts may be assembled in two or more different axial positions with respect to each other. For example the outer part may comprise three sets of intruded ring cavities that are to cooperate with two sets of fins provided at the inner part. The inner part may be inserted in the outer part in such a way that the two sets of fins of the inner part engage with the first and the second set of intruded ring cavities of the outer part such that a mouthpiece with a first configuration is obtained. Alternatively, the inner part may be inserted such that the two sets of fins of the inner part engage with the second and third set of intruded ring cavities of the outer part such that a mouthpiece with a second configuration is obtained. The dimensions of the airflow channels formed within the mouthpiece in the first and in the second configuration differ from each other. Accordingly, a mouthpiece with adjustable characteristics in terms of airflow management and overall aerosolization performance is obtained.

In the above example the inner part may be arranged in two pre-defined axial positions with respect to the outer part of the mouthpiece. By providing additional sets of interlocking structures, additional pre-defined axial positions of the inner part with respect to the outer part may be established. In this way versatility of the corresponding mouthpiece can be further increased.

Depending on how deep the inner part is inserted into the outer part, the size of the volumetric recess formed at the outlet end of the mouthpiece may vary. This volumetric recess acts as a final expansion chamber before the aerosol is inhaled by the consumer. It does thus contribute to the overall homogenization and cooling properties of the mouthpiece. If the inner part is inserted into the outer part to a small extend only, a smaller volumetric recess is formed. If the inner part is inserted into the outer part to a greater extend, a larger volumetric recess is formed.

The interlocking structures may comprise additional sets of interlocking structures, such that the two main parts may be assembled in two or more different axial positions with respect to each other, and the and inner part may be axially inserted from the outlet end side into the outer part. This allows to reposition the inner part of the mouthpiece between the two or more axial positions in an assembled state where the mouthpiece is attached to an aerosol-generating article. This enables an easy repositioning of the inner part of the mouthpiece. This enables easy handling for a user.

The mouthpiece of the present invention may be used with any kind of aerosol-generating device or aerosol-generating article. In this regard, the inlet end of the mouthpiece may comprise a connection portion configured to attach the mouthpiece to such aerosol-generating device or an aerosol-generating article.

The connection portion may employ any suitable mechanism that allows a user to removably attach the mouthpiece to an aerosol-generating device or an aerosol-generating article. For example, the connection portion can be a male/female coupling. The male/female coupling may be correspondingly shaped coupling elements which are configured to provide a friction-fit or form-fit connection.

A friction-fit connection may be established by the coupling elements having corresponding shape that can be inserted into each other and that are maintained in the connected position by friction between the coupling elements.

A form-fit connection may be obtained by providing the coupling elements with threaded portions forming a screwed joint. Such coupling elements may include 90° male/female fittings that are quickly and reliable attached to each other by 90° rotation of the coupling elements. Of course also coupling elements including higher rotation angles may be employed. Male/female screw couplings enable reliable and leak free connections and allow for hermetic fastening of the mouthpiece to an aerosol-generating device or an aerosol-generating article.

The connection portion may be configured as a pharma or medical device type coupling. Pharma or medical device type couplings additionally may increase integrity of the generated aerosol.

In a further aspect of the present invention there is provided an aerosol-generating system comprising a mouthpiece as described above and an aerosol generating device or an aerosol-generating article. The mouthpiece and the aerosol-generating device or the aerosol-generating article have corresponding connection portions to removably attach the mouthpiece to the aerosol-generating device or the aerosol-generating article. The aerosol generating device or the aerosol-generating article can be any of the currently available aerosol generating devices or aerosol-generating articles including but not limited to heat not burn products (HNB) or vaping systems, in which liquid substrate is aerosolized.

In a further aspect of the present invention there is provided a method for assembling a mouthpiece. The method includes providing an outer part, wherein the outer part forms a central inner channel and a tubular outer wall of the mouthpiece. The method further includes providing an inner part, wherein the inner part has a hollow tubular shape with a side wall, one open end face and one closed end face. The mouthpiece is obtained by inserting the inner part in an axial direction into the outer part such that the side wall of the inner part is located between the central channel and the outer wall of the outer part.

The inner part and the outer part used in the method for forming a mouthpiece may correspond to the inner part and the other part as described above. In particular, these parts may be provided with interlocking structures such that upon assembly thereof a mouthpiece with predefined dimensions and predefined airflow path is obtained.

Features described in relation to one aspect may equally be applied to other aspects of the invention.

BRIEF DESCRIPTION OF THE DRAWINGS

The invention will be further described, by way of example only, with reference to the accompanying drawings in which.

DETAILED DESCRIPTION OF THE DRAWINGS

Figure 1:
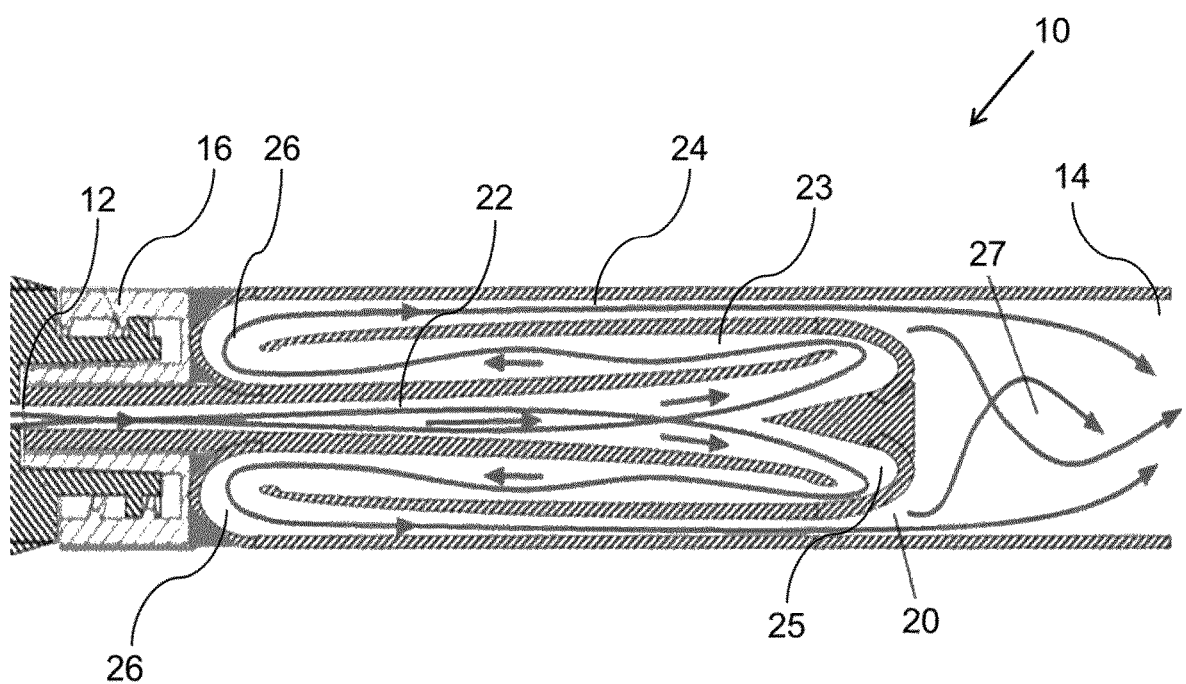
FIG. 1 shows a mouthpiece according to the invention.

In FIG. 1 a mouthpiece 10 according to the present invention is depicted. The mouthpiece is of tubular shape and defines an airflow path 20 between the inlet end 12 and the outlet end 14. In FIG. 1 the inlet end 12 is provided at the left-hand side of the mouth piece 10 and is provided with a connection portion 16 for connecting the mouthpiece 10 to an aerosol-generating device. The outlet end 14 is provided at the opposite end of the inlet end 12 of mouthpiece 10 and is configured to be taken into the mouth by a user for inhalation.

The airflow path 20 between the inlet end 12 and the outlet end 14 comprises a plurality of concentrically and coaxially arranged tubular channels 22, 23, 24 that are arranged such that the airflow direction is reversed twice before the aerosol is exiting the mouthpiece 10 at the outlet end 14.

The mouthpiece 10 comprises a central channel 22 that extends from the inlet end 12 and that extends towards the outlet end 14 of the mouthpiece. The central channel 22 radially diverges along the direction of the aerosol flow. In other words the diameter of the central channel 22 increases along the direction of the aerosol flow. At the end of the central channel 22 the flow direction of the aerosol is inverted and the aerosol is further guided through co-axially arranged intermediate tubular channel 23 towards the inlet end 12 of the mouthpiece 10. At the end of intermediate channel 23 the flow direction of the aerosol is again inverted and the aerosol is guided through co-axially arranged outer tubular channel 24 towards the outlet end 14 of the mouthpiece 10. The aerosol is finally discharged through the outlet end 14 for inhalation by the consumer.

With the design of the present invention, the length of the airflow path 20 through the mouthpiece 10 is effectively elongated, such that additional time for dissipating thermal energy is available. In addition, expansion chambers 25, 26 are formed at the reversal points between consecutive channels 22, 23, 24. These expansion chambers 25, 26 assist in cooling and homogenization of the aerosol. Recess 27 at the outlet end of the mouthpiece 10 also acts as an expansion chamber that assists in cooling and homogenization of the aerosol. The recess 27 may be defined by the part of the inner wall of the mouthpiece 10 at the outlet end and the end face 46 that is set further back than the aperture at the outlet end. The expansion chamber may be defined by a part of an inner wall of the mouthpiece 10 at the outlet end, the end face 46 and an aperture at the outlet end.

The mazelike airflow path 20 of the mouthpiece 10 is suitably obtained by manufacturing the mouthpiece 10 from two parts as indicated in FIG. 2A. The first or outer part 30 of the mouthpiece 10 is depicted on the left-hand side of FIG. 2a and defines the inlet 32, the connection portion 34, the central channel 22 and a tubular outer wall 36 of the mouthpiece 10. The inner part 40 of the mouthpiece 10 is generally U-shaped. It has a hollow tubular shape with a side wall 42, one open end face 44 and one closed end face 46. The inner part 40 is formed such that it can be axially inserted with its open end face 44 into the outer part 30 of the mouthpiece 10. When fully assembled, the side wall 42 of the inner part 40 is located between the central channel 22 and the outer wall 36 of the outer part 30.

The two main parts 30, 40 of the mouthpiece 10 have corresponding interlocking structures 50 that engage with each other when the mouthpiece 10 is fully assembled. The interlocking structures 50 are formed such that they maintain the mouthpiece 10 in the fully assembled configuration during the user experience. The interlocking structures 50 further ensure that a mouthpiece 10 with predetermined dimensions is obtained.

Figure 2:
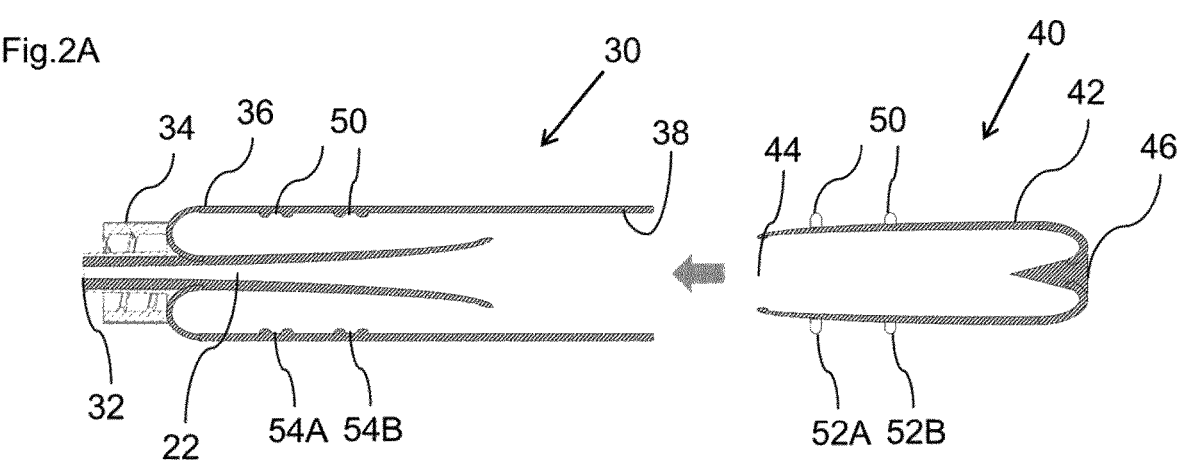
FIG. 2 shows a two-part mouthpiece according to the invention.
Figure 2:
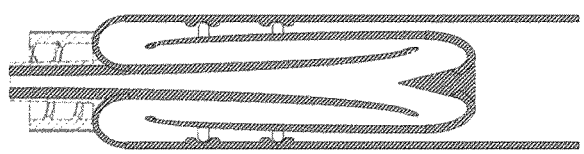

In the embodiment depicted in FIG. 2, the inner part 40 of the mouthpiece 10 comprises protruding fins 52 provided at the outer circumference of the side wall 42 of the inner part 40. The outer part 30 comprises corresponding intruded ring cavities 54, which are provided to the inner surface 38 of the outer wall 36 of the outer part 30. In the fully assembled state, the protruding fins 52 of the inner part 40 engage with the intruded ring cavities 54 of the other part 30, as depicted in FIG. 2B. Inner and outer parts 40, 30 of the mouthpiece 10 each comprise two sets of fins 52A, 52B and intruded ring cavities 54A, 54B, respectively, that are axially spaced from each other. Each set of fins 52A, 52B consists of three or more fins 52 that are equidistantly distributed over the circumference of the side wall 36 of the inner part 30. Correspondingly, each set of intruded ring cavities 54A, 54B consists of three or more intruded ring cavities 54 that are equidistantly distributed over the inner surface 38 of the outer wall 36 of the outer part 30.

Figure 3:
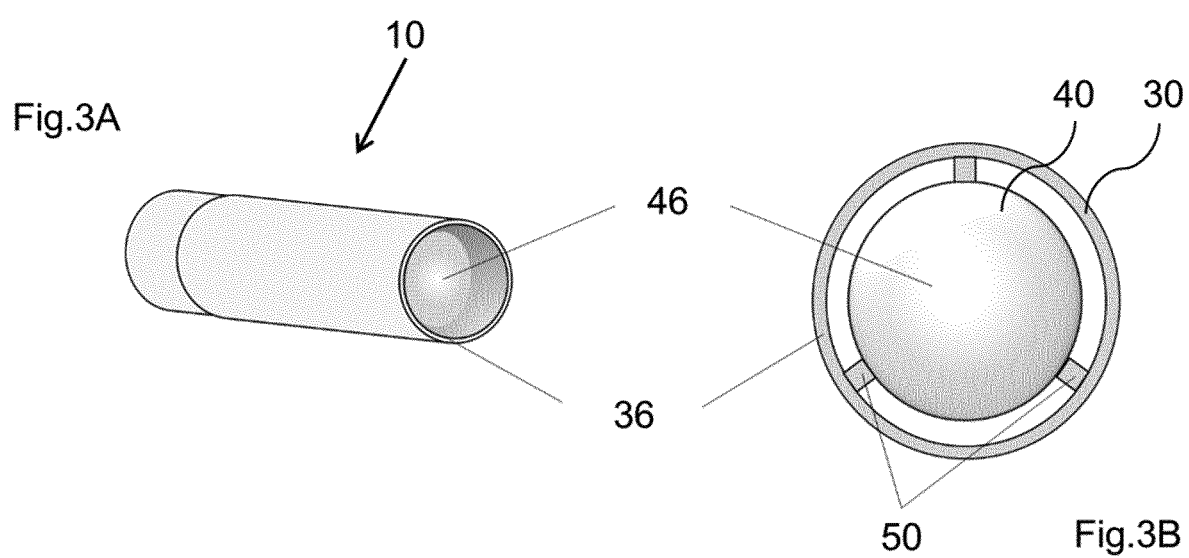
FIG. 3 shows a 3D view and a plan view of the outlet end of the mouthpiece of FIG. 1.

FIG. 3 shows a perspective view and a side view of a mouthpiece 10 according to the present invention. In the perspective view of FIG. 3A the tubular overall shape of the mouthpiece 10 and the spherical shape of the closed end face 46 of the inner part 40 can be seen. The side view of FIG. 3B shows the circumferential distribution of a set of interlocking structures 50 consisting of three elements which are equidistantly distributed.

Figures 4, 4A, 4B:
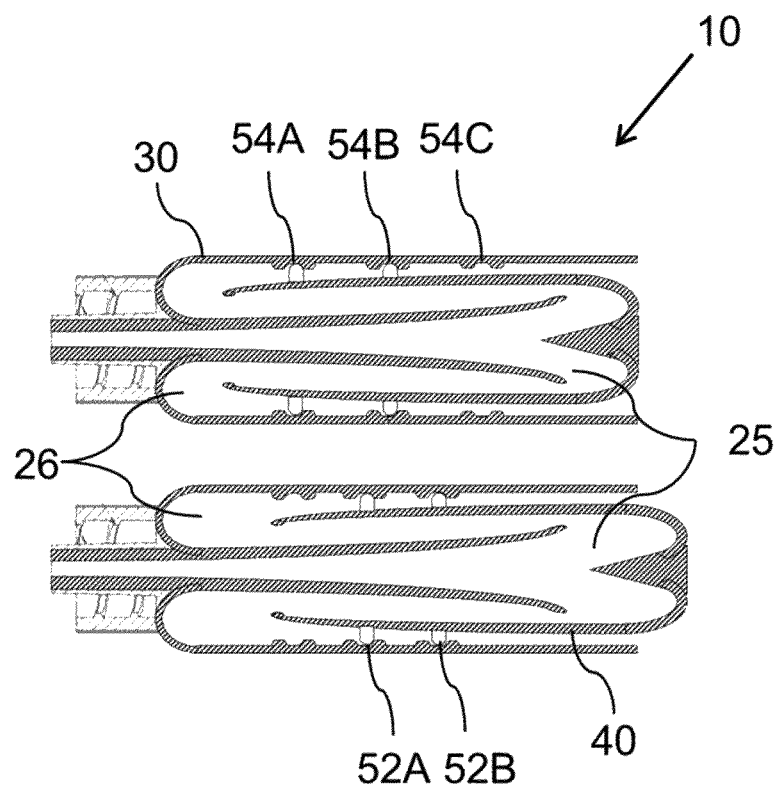
FIG. 4 shows a modification of the mouthpiece of FIG. 2.

FIG. 4 relates to a modification of the mouthpiece of FIG. 3, wherein the outer part 30 of the mouthpiece 10 comprises three sets of intruded ring cavities 54. The mouthpiece 10 may be assembled either according to FIG. 4A, in which the two sets of fins 52A, 52B engage with the first and the second set of intruded ring cavities 54A, 54B and in which the inner part 40 is inserted into the outer part 30 as far as possible. Alternatively, the two sets of fins 52A, 52B may also engage with the second and the third set of intruded ring cavities 54B, 54C as depicted in FIG. 4B. In the latter configuration, the inner part 40 is inserted to a lesser extent into the outer part 30 with the consequence that the expansion chambers 25, 26 within the mouthpiece 10 are enlarged. Depending on which modification is chosen, the mouthpiece 10 shows different air-management characteristics and yields different aerosolization results. The user may choose a suitable modification depending on environmental conditions or on personal preferences.

Figure 5:
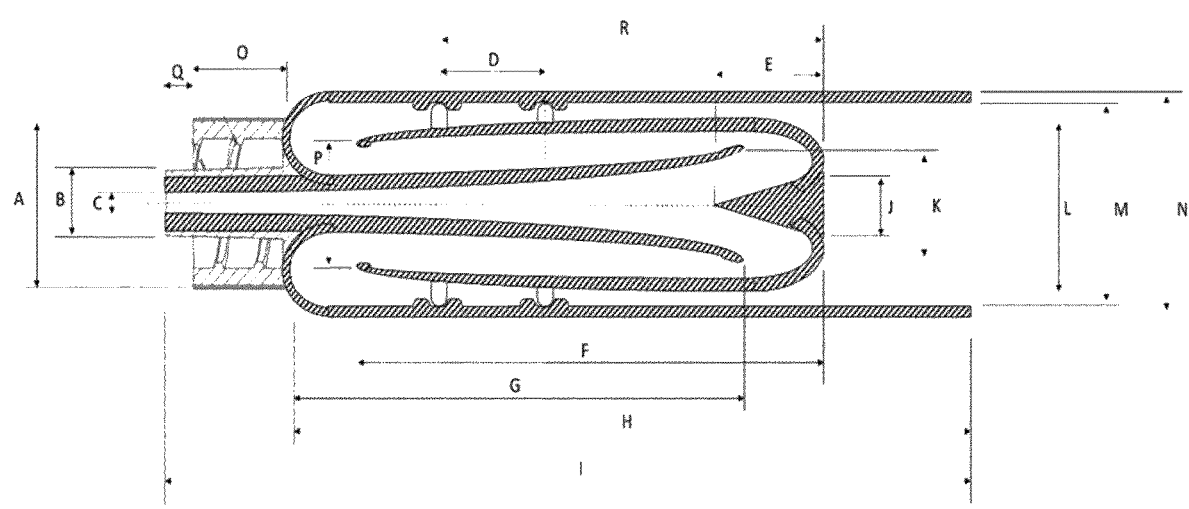
FIG. 5 shows dimensions of the mouthpiece of FIG. 2.

Both parts 30, 40 of the mouthpiece 10 depicted in the figures are formed from thermoplastic polyester elastomers with food grade polymeric compounds to be used under Good Manufacturing Practice. FIG. 5 again shows the inner and the outer part of a mouthpiece and preferential ranges for the dimensions indicated in FIG. 5 are listed in table 1 below.

| Dimensions | Ranges (mm) | |
| --- | --- | --- |
| | Range | Preferred Range |
| A | 3.5 to 9 | 4 to 7 |
| B | 3 to 7 | 4 to 5 |
| C | 0.5 to 5 | 2 to 4 |
| D | 3 to 14 | 4 to 7 |
| E | 3 to 11 | 3 to 7 |
| F | 8 to 23 | 11 to 21 |
| G | 9 to 25 | 13 to 21 |
| H | 0.05 to 0.4 | 0.15 to 0.35 |
| I | 21 to 45 | 25 to 35 |
| J | 3 to 8 | 4 to 7 |
| K | 4 to 9 | 5 to 8 |
| L | 1 to 7 | 2 to 5 |
| M | 4 to 11 | 4.5 to 8.5 |
| N | 5 to 12 | 5 to 9 |
| O | 4 to 13 | 5 to 9 |
| Q | 1 to 4 | 1 to 3 |
| R | 6 to 21 | 13 to 18 |

Figure 6:
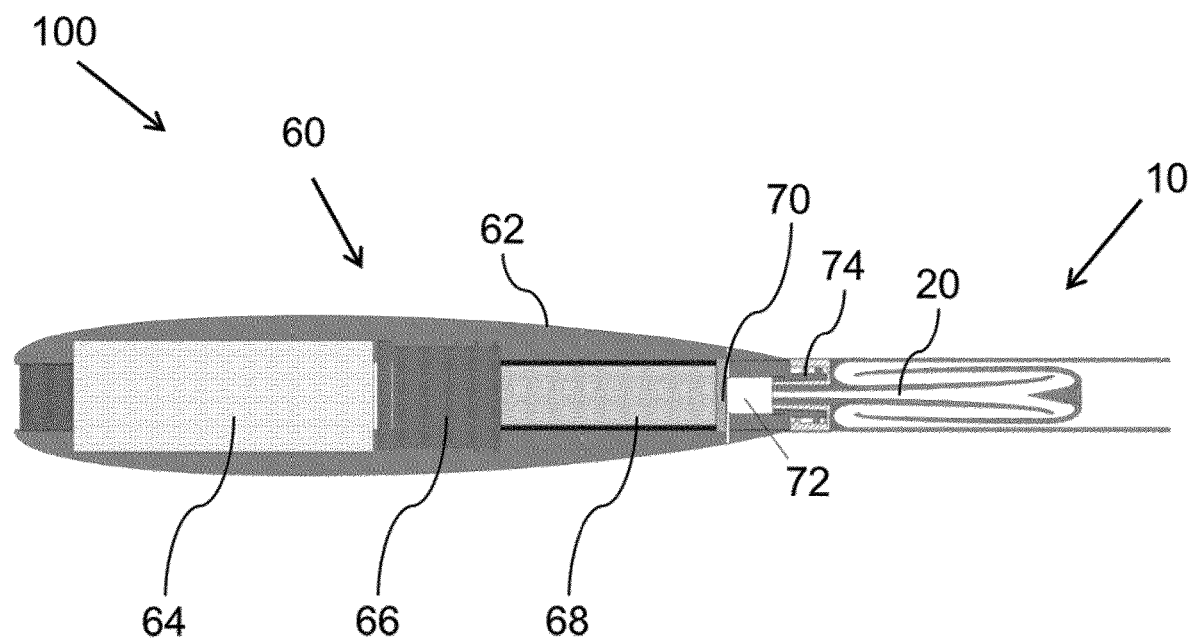
FIG. 6 shows an aerosol-generating device with a mouthpiece of FIG. 1

FIG. 6 shows an aerosol-generating system 100 comprising an aerosol-generating device 60 and a mouthpiece 10 as described above. The aerosol-generating device 60 comprises a housing 62 with a power source 64, control electronics 66, an aerosol-forming substrate 68 and an aerosol-generation unit 70. The aerosol-generation unit 70 includes an aerosol-forming chamber 72 which is provided at one end of the aerosol-generating device 60. This end of the aerosol-generating device 60 further comprises a connection portion 74 to which a mouthpiece 10 as described above can be connected. When the mouthpiece 10 is connected to aerosol-generating device 60, an airflow path 20 from the aerosol-forming chamber 72 through the mouthpiece 10 is established. During a user experience, a user may inhale the aerosol created in the aerosol-forming chamber 72 through the mouthpiece 10.

The invention claimed is:

1. A mouthpiece for an aerosol-generating article, the mouthpiece comprising:
    an inlet end, configured to allow an aerosol to flow into the mouthpiece,
    an outlet end, configured to allow the aerosol to flow out of the mouthpiece, and an aerosol flow path extending between the inlet end and the outlet end, wherein the mouthpiece is formed such that the flow direction of the aerosol is reversed at least once between the inlet end and the outlet end, and wherein the mouthpiece is formed from an outer part and an inner part, wherein the outer part forms a central inner channel and a tubular outer wall of the mouthpiece, and wherein the inner part has a hollow tubular shape with a side wall, one open end face and one closed end face, wherein the inner part is axially inserted from the outlet end side into the outer part in such a way that the side wall of the inner part is located between the central channel and the tubular outer wall of the outer part.

2. The mouthpiece according to claim 1, wherein the inlet end of the mouthpiece comprises a connection portion configured to attach the mouthpiece to an aerosol-generating device.

3. The mouthpiece according to claim 1, wherein the aerosol flow path includes a plurality of expansion chambers.

4. The mouthpiece according to claim 1, wherein the aerosol flow path includes a plurality co-axially arranged tubular channels.

5. The mouthpiece according to claim 1, wherein the mouthpiece comprises a cavity recessed from the outlet end of the mouthpiece.

6. The mouthpiece according to claim 1, wherein the mouthpiece comprises a ring shaped outlet end.

7. The mouthpiece according to claim 1, wherein the mouthpiece comprises a central channel that extends from the inlet end and that radially diverges along the direction of the aerosol flow, and wherein the mouthpiece further comprises at least two tubular channels that are co-axially arranged with respect to the central channel and that are in fluid communication with the central channel.

8. The mouthpiece according to claim 4, wherein the aerosol flow direction is reversed between each of the consecutively arranged aerosol flow channels.

9. The mouthpiece according to claim 1, wherein the two main parts of the mouthpiece have corresponding interlocking structures that engage with each other such that a mouthpiece with predetermined dimensions is obtained.

10. The mouthpiece according to claim 9, wherein the interlocking structures comprise one or more, preferably three, fins and one or more, preferably three, intruded ring cavities that are provided at opposing surfaces of the main parts of the mouthpiece.

11. An aerosol-generating system comprising an aerosol-generating device and the mouthpiece according to claim 1.

12. The aerosol-generating system according to claim 11, wherein the aerosol-generating device and the mouthpiece comprise corresponding connection portions, such that the mouthpiece is removably attachable to the aerosol-generating device.

13. A method for assembling a mouthpiece, comprising the steps of:
(a) providing an outer part, wherein the outer part forms a central inner channel and a tubular outer wall of the mouthpiece,
(b) providing an inner part, wherein the inner part has a hollow tubular shape with a side wall, one open end face and one closed end face,
(c) inserting the inner part in an axial direction from the outlet end side into the outer part such that the side wall of the inner part is located between the central channel and the outer wall of the outer part.

* * * * *